(12) United States Patent
Lukas et al.

(10) Patent No.: US 7,947,661 B2
(45) Date of Patent: May 24, 2011

(54) COMPOUNDS FOR THE TREATMENT OF MARIHUANA DEPENDENCE, WITHDRAWAL, AND USAGE

(75) Inventors: Scott E. Lukas, Boxboro, MA (US); Perry F. Renshaw, Bedford, MA (US)

(73) Assignee: The McLean Hospital Corporation, Belmont, MA (US)

( * ) Notice: Subject to any disclaimer, the term of this patent is extended or adjusted under 35 U.S.C. 154(b) by 731 days.

(21) Appl. No.: 11/659,924

(22) PCT Filed: Aug. 10, 2005

(86) PCT No.: PCT/US2005/028407
§ 371 (c)(1), (2), (4) Date: Sep. 18, 2007

(87) PCT Pub. No.: WO2006/020703
PCT Pub. Date: Feb. 23, 2006

(65) Prior Publication Data
US 2008/0300214 A1    Dec. 4, 2008

Related U.S. Application Data

(60) Provisional application No. 60/600,481, filed on Aug. 11, 2004.

(51) Int. Cl.
*A01N 43/04* (2006.01)
*A61K 31/70* (2006.01)

(52) U.S. Cl. ............... 514/49; 514/42; 514/43; 514/50; 514/51

(58) Field of Classification Search .................. None
See application file for complete search history.

(56) References Cited

U.S. PATENT DOCUMENTS

| | | | |
|---|---|---|---|
| 3,873,698 A * | 3/1975 | Penn ............................. | 514/49 |
| 4,027,017 A | 5/1977 | Hata et al. | |
| 4,048,316 A | 9/1977 | Penn | |
| 4,115,576 A | 9/1978 | Penn | |
| 4,386,077 A | 5/1983 | Borgo | |
| 4,569,929 A | 2/1986 | Growdon et al. | |
| 4,704,361 A | 11/1987 | Miccoli et al. | |
| 4,764,603 A | 8/1988 | Zappia et al. | |
| 4,999,382 A | 3/1991 | Wurtman et al. | |
| 5,179,126 A | 1/1993 | Wurtman et al. | |
| 5,278,176 A | 1/1994 | Lin | |
| 5,409,946 A | 4/1995 | Garvey et al. | |
| 5,472,958 A | 12/1995 | Gunn, Jr. et al. | |
| 5,635,486 A | 6/1997 | Yamamoto et al. | |
| 5,691,320 A | 11/1997 | von Borstel et al. | |
| 5,691,365 A | 11/1997 | Crooks et al. | |
| 5,888,532 A | 3/1999 | Pritsos et al. | |
| 5,919,789 A | 7/1999 | Dyke et al. | |
| 5,958,896 A | 9/1999 | Renshaw et al. | |
| 5,977,174 A | 11/1999 | Bradley et al. | |
| 6,103,703 A | 8/2000 | Renshaw et al. | |
| 6,132,724 A | 10/2000 | Blum | |
| 6,153,653 A | 11/2000 | Shashoua | |
| 6,258,794 B1 | 7/2001 | Renshaw | |
| 6,277,855 B1 | 8/2001 | Yerxa | |
| 6,284,268 B1 | 9/2001 | Mishra et al. | |
| 6,319,953 B1 | 11/2001 | Carlson et al. | |
| 6,331,568 B1 | 12/2001 | Horrobin | |
| 6,410,522 B1 | 6/2002 | Ruenberg | |
| 6,503,951 B2 | 1/2003 | Pischel et al. | |
| 6,541,043 B2 | 4/2003 | Lang | |
| 6,608,064 B2 | 8/2003 | McLean et al. | |
| 6,624,195 B2 | 9/2003 | Horrobin | |
| 6,696,495 B2 | 2/2004 | Mueller | |
| 6,706,764 B2 | 3/2004 | Kaddurah-Daouk et al. | |
| 6,727,231 B1 | 4/2004 | Page et al. | |
| 6,852,870 B2 | 2/2005 | Stoll | |
| 6,989,376 B2 | 1/2006 | Watkins et al. | |
| 7,026,301 B2 | 4/2006 | Cardozo et al. | |
| 7,053,064 B2 * | 5/2006 | Lukas ............................. | 514/51 |
| 7,601,701 B2 * | 10/2009 | Lukas ............................. | 514/45 |
| 2002/0019364 A1 | 2/2002 | Renshaw | |
| 2002/0028787 A1 | 3/2002 | Watkins et al. | |
| 2002/0182196 A1 | 12/2002 | McCleary | |
| 2003/0100844 A1 | 5/2003 | Miller et al. | |
| 2003/0114415 A1 | 6/2003 | Wurtman et al. | |
| 2003/0220291 A1 | 11/2003 | Renshaw | |
| 2003/0224435 A1 | 12/2003 | Seiwert | |
| 2003/0232827 A1 | 12/2003 | Meltzer et al. | |
| 2004/0102419 A1 | 5/2004 | Kaddurah-Daouk et al. | |
| 2004/0167093 A1 | 8/2004 | Lukas | |
| 2004/0176316 A1 | 9/2004 | Renshaw et al. | |
| 2004/0192732 A1 * | 9/2004 | Pratt et al. ..................... | 514/319 |
| 2004/0266659 A1 | 12/2004 | LaBerge | |

(Continued)

FOREIGN PATENT DOCUMENTS

DE    3400276    7/1985

(Continued)

OTHER PUBLICATIONS

U.S. Appl. No. 12/704,964, filed Feb. 12, 2010, Renshaw et al.

(Continued)

*Primary Examiner* — Traviss C McIntosh, III
(74) *Attorney, Agent, or Firm* — Clark & Elbing LLP (57) ABSTRACT

The invention provides methods for treating or suppressing marihuana usage, withdrawal, or dependence involving administration of a therapeutically-effective amount of a cytosine-containing or cytidine-containing compound, uridine-containing compound, creatine-containing compound, adenosine-containing, or adenosine-elevating compound to a mammal.

19 Claims, 1 Drawing Sheet

U.S. PATENT DOCUMENTS

| | | | |
|---|---|---|---|
| 2005/0113449 | A1 | 5/2005 | Renshaw |
| 2005/0129710 | A1 | 6/2005 | Renshaw et al. |
| 2006/0128671 | A1 | 6/2006 | Kaddurah-Daouk et al. |
| 2008/0132472 | A1 | 6/2008 | Renshaw |
| 2009/0054370 | A1 | 2/2009 | Renshaw |
| 2009/0215714 | A1 | 8/2009 | Renshaw et al. |
| 2010/0041620 | A1 | 2/2010 | Renshaw et al. |
| 2010/0041621 | A1 | 2/2010 | Renshaw et al. |
| 2010/0197628 | A1 | 8/2010 | Renshaw et al. |

FOREIGN PATENT DOCUMENTS

| | | |
|---|---|---|
| EP | 0 188 647 | 7/1986 |
| EP | 0 218 190 | 4/1987 |
| EP | 0 431 758 | 6/1991 |
| EP | 0 615 750 | 9/1994 |
| JP | 63-208524 | 8/1988 |
| JP | 2-500372 | 2/1990 |
| JP | 4-18034 | 1/1992 |
| JP | 8-183737 | 7/1996 |
| RU | 2003332 | 11/1993 |
| RU | 2128653 | 4/1999 |
| WO | WO 89/03837 | 5/1989 |
| WO | WO 93/14076 | 7/1993 |
| WO | WO 99/26620 | 6/1999 |
| WO | WO 00/06174 | 2/2000 |
| WO | WO 00/11952 | 3/2000 |
| WO | WO 01/28528 | 4/2001 |
| WO | WO 01/44265 | 6/2001 |
| WO | WO 01/72288 | 10/2001 |
| WO | WO 02/45583 | 6/2002 |
| WO | WO 02/088159 | 11/2002 |
| WO | WO 03/082211 | 10/2003 |
| WO | WO 2005/086619 | 9/2005 |

OTHER PUBLICATIONS

U.S. Appl. No. 12/778,637, filed May 12, 2010, Renshaw.
Adibhatla et al., "Citicoline Mechanisms and Clinical Efficacy in Cerebral Ischemia," *J. Neurosci. Res.* 70:133-139, 2002.
Agnoli et al., "Efficacy of CDPcholine in Chronic Cerebral Vascular Diseases (CCVD)," *Proceedings of the International Meeting on Novel Biochemical, Pharmacological and Clinical Aspects of Cytidinediphosphocholine*, Sorrento, Italy, Jun. 12-14, 1984, pp. 305-315.
Ågren et al., "Creatinine and Creatine in CSF: Indices of Brain Energy Metabolism in Depression. Short Note," *J. Neural. Transm.* 74:55-59, 1988.
Agut et al., "Cytidine(5')Diphosphocholine Enhances the Ability of Haloperidol to Increase Dopamine Metabolites in the Striatum of the Rat and to Diminish Stereotyped Behavior Induced by Apomorphine," *Neuropharmacology* 23:1403-1406, 1984.
Alvarado et al., "1H Magnetic Resonance Spectroscopy (MRS) Assessment of the Effects of Eicosapentaenoic-Docosahexaenoic Acids and Choline-Inositol Supplementation on Children with Attention Deficit Hyperactivity Disorder (ADHD)," *VITAE Academia Biómedica Digital* Jul.-Sep. 2004 N°20 [Available at http://vitae.ucv.ve/?rv=68] (pp. 1-18).
Alvarez et al., "Double-Blind Placebo-Controlled Study with Citicoline in APOE Genotyped Alzheimer's Disease Patients. Effects on Cognitive Performance, Brain Bioelectrical Activity and Cerebral Perfusion," *Methods Find. Exp. Clin. Pharmacol.* 21:633-644, 1999. (Abstract).
Ambrosini et al., "Antidepressant Treatments in Children and Adolescents: II. Anxiety, Physical, and Behavioral Disorders," *J. Am. Acad. Child Adolesc. Psychiatry* 32:483-493, 1993.
American Psychiatric Association, "Diagnostic and Statistical Manual of Mental Disorders: DSM-IV," *American Psychiatric Association* (Washington, D.C.), Entry for "Mood Episodes" and "Depressive Disorders," pp. 320-327, 339-349, 718, 1994.
American Psychiatric Association, "Diagnostic and Statistical Manual of Mental Disorders: DSM-IV," *American Psychiatric Association* (Washington, D.C.), Entry for "Substance Dependence Criteria," pp. 181-183, 1994.

Andreazza et al., "Oxidative Stress Markers in Bipolar Disorder: A Meta-Analysis," *J. Affect. Disord.* 111:135-144, 2008.
Babb et al., "Differential Effect of CDP-Choline on Brain Cytosolic Choline Levels in Younger and Older Subjects as Measured by Proton Magnetic Resonance Spectroscopy," *Psychopharmacology* 127:88-94, 1996.
Beers et al., "The Merck Manual of Diagnosis and Therapy," *Merck & Co, Inc., 17th Edition*, Chapter 173: Sleeping Disorders, pp. 1409-1414, 1999.
Biederman et al., "Non-Stimulant Treatments for ADHD," *Eur. Child Adolesc. Psychiatry* 9:I51-I59, 2000.
Bishopp, "Interneuron's Citicoline Works for Moderate to Severe Stroke," *BioWorld Today*, Jul. 17, 1997, p. 3.
Boudouresques et al., "Therapeutic Conduct in Light of a Cerebral Vascular Accident and the Use of CDP-Choline," *International Symposium: Brain Suffering and Precursors of Phospholipids*, pp. 1-13, 1980.
Bronk et al., "The Transport and Metabolism of Naturally Occurring Pyrimidine Nucleosides by Isolated Rat Jejunum," *J. Physiol.* 395:349-361, 1988.
Brown et al., "CNS Complications of Cocaine Abuse: Prevalence, Pathophysiology, and Neuroradiology," *Am. J. Roentgenol.* 159:137-147, 1992.
Budney et al., "Marijuana Abstinence Effects in Marijuana Smokers Maintained in Their Home Environment," *Arch. Gen. Psychiatry* 58:917-924, 2001.
Carlezon Jr. et al., "Antidepressant-Like Effects of Cytidine in the Forced Swim Test in Rats," *Biol. Psychiatry* 51:882-889, 2002.
Carlezon Jr. et al., "Antidepressant-Like Effects of Uridine and Omega-3 Fatty Acids are Potentiated by Combined Treatment in Rats," *Biol. Psychiatry* 57:343-350, 2005.
Carlezon Jr. et al., "Behavioral Effects of Citicoline (CDP-Choline) and Metabolites in Rats," Poster No. 67, Scottsdale, AR: Annual Meeting for the College on Problems of Drug Dependence, Jun. 18, 2001. (Abstract).
Castañé et al., "Lack of CB1 Cannabinoid Receptors Modifies Nicotine Behavioural Responses, But Not Nicotine Abstinence," *Neuropharmacology* 43:857-867, 2002.
Centrone et al., "Use of Citicoline in High Dosages in Acute Cerebrovascular Disease," *Minerva Med.* 77:371-373, 1986. (Abstract).
Chang et al., "Neurochemical Alterations in Asymptomatic Abstinent Cocaine Users: A Proton Magnetic Resonance Spectroscopy Study," *Biol. Psychiatry* 42:1105-1114, 1997.
Christensen et al., "Abnormal Cerebral Metabolism in Polydrug Abusers During Early Withdrawal: A 31P MR Spectroscopy Study," *Magn. Reson. Med.* 35:658-663, 1996.
Cohen et al., "Decreased Brain Choline Uptake in Older Adults. An In Vivo Proton Magnetic Resonance Spectroscopy Study," *JAMA* 274:902-907, 1995.
Cohrs et al., "Sleep and Acetylcholine-Precursor-Substances," *Pharmacopsychiatry* 28:169, 1995 (Abstract).
Connolly et al., "Uridine and Its Nucleotides: Biological Actions, Therapeutic Potentials," *Trends Pharmacol. Sci.* 20:218-225, 1999.
Cyr et al., "Current Drug Therapy Recommendations for the Treatment of Attention Deficit Hyperactivity Disorder," *Drugs* 56:215-223, 1998.
Daly et al., "The Use of Tricyclic Antidepressants in Children and Adolescents," *Pediatr. Clin. North Am.* 45:1123-1135, 1998.
De Rosa et al., "Pharmacokinetics and Metabolism of Double-Labeled CDP Choline," Proceedings of the International Meeting on Novel Biochemical, Pharmacological and Clinical Aspects of Cytidinediphosphocholine, Sorrento, Italy, Jun. 12-14, 1984, pp. 139-157.
Elia, "Stimulants and Antidepressant Pharmacokinetics in Hyperactive Children," *Psychopharmacol. Bull.* 27:411-415, 1991.
Emslie et al., "Nontricyclic Antidepressants: Current Trends in Children and Adolescents," *J. Am. Acad. Child Adolesc. Psychiatry* 38:517-528, 1999.
English et al., "Elevated Frontal Lobe Cytosolic Choline Levels in Minimal or Mild AIDS Dementia Complex Patients: A Proton Magnetic Resonance Spectroscopy Study," *Biol. Psychiatry* 41:500-502, 1997.

Fernández, "Efficacy and Safety of Oral CDP-Choline: Drug Surveillance Study in 2817 Cases," *Arzneim.-Forsch.* 33:1073-1080, 1983.

Fioravanti et al., "Cytidinediphosphocholine (CDP-Choline) for Cognitive and Behavioural Disturbances Associated with Chronic Cerebral Disorders in the Elderly," *Cochrane Database Syst. Rev.* Apr. 18, 2005 (2):CD000269.

Forester et al., "31Phosphorus Magnetic Resonance Spectroscopy Study of Tissue Specific Changes in High Energy Phosphates Before and After Sertraline Treatment of Geriatric Depression," *Int. J. Geriatr. Psychiatry* 24:788-797, 2009.

Frey et al., "Myo-Inositol in Depressive and Healthy Subjects Determined by Frontal 1H-Magnetic Resonance Spectroscopy at 1.5 Tesla," *J. Psychiatr. Res.* 32:411-420, 1998.

Fux et al., "A Placebo-Controlled Cross-Over Trial of Adjunctive EPA in OCD," *J. Psychiatr. Res.* 38:323-325, 2004.

G.-Coviella et al., "Effect of Cytidine(5')Diphosphocholine (CDP-Choline) on the Total Urinary Excretion of 3-Methoxy-4-Hydroxyphenylglycol (MHPG) by Rats and Humans," *J. Neural Transm.* 66:129-134, 1986.

G.-Coviella et al., "Metabolism of Cytidine(5')-Diphosphocholine (CDP-Choline) Following Oral and Intravenous Administration to the Human and the Rat," *Neurochem. Int.* 11:293-297, 1987.

G.-Coviella et al., "Enhancement by Cytidine of Membrane Phospholipid Synthesis," *J. Neurochem.* 59:338-343, 1992.

Gallai et al., "Study of the P300 and Cerebral Maps in Subjects With Multi-Infarct Dementia Treated With Cytidine," *Psychopharmacology* 103:1-5, 1991.

Galletti et al., "Biochemical Rationale for the Use of CDPcholine in Traumatic Brain Injury: Pharmacokinetics of the Orally Administered Drug," *J. Neurol. Sci.* 103:S19-S25, 1991.

Geiger et al., "Cytidine and Uridine Requirement of the Brain," *J. Neurochem.* 1:93-100, 1956.

Giménez et al., "Changes in Brain Striatum Dopamine and Acetylcholine Receptors Induced by Chronic CDP-Choline Treatment of Aging Mice," *Br. J. Pharmacol.* 104:575-578, 1991.

Goodman and Gilman's, "The Pharmacological Basis of Therapeutics, 10$^{th}$ Ed.," *McGraw-Hill Medical Publishing Division*, pp. 54-56, 2001.

Grau et al., "Study on the Protection of CDP-Choline Against Nicotine Intoxication," *Arzneim.-Forsch.* 33:1025-1026, 1983.

Greenberg, "Clinical Dimensions of Fatigue," *Prim. Care Companion J. Clin. Psychiatry* 4:90-93, 2002.

Greenwell, "Enhancing Cognitive Function: Keeping Your Memory in Tip Top Shape," LE (Life Extension) Magazine, 2000. [Available at www.lef.org/magazine/mag2000/may00-cover-html.].

Hansen, "Blood Nucleoside and Nucleotide Studies in Mental Disease," *Br. J. Psychiatry.* 121:341-350, 1972.

HD Blog, "Triacetyluridine. Health Care & Huntington's Disease News," www.huntington.info, Dec. 3, 2003. (pp. 1-3).

Higgins, "A Comparative Analysis of Antidepressants and Stimulants for the Treatment of Adults with Attention-Deficit Hyperactivity Disorder," *J. Fam. Pract.* 48:15-20, 1999.

Hoff et al., "Effects of Crack Cocaine on Neurocognitive Function," *Psychiatry Res.* 60:167-176, 1996.

Honda et al., "Sleep-Promoting Effects of Intraperitoneally Administered Uridine in Unrestrained Rats," *Neurosci. Lett.* 62:137-141, 1985.

Inoué et al., "Differential Sleep-Promoting Effects of Five Sleep Substances Nocturnally Infused in Unrestrained Rats," *Proc. Natl Acad. Sci. U S A.* 81:6240-6244, 1984.

Interneuron Pharmaceuticals, Inc., "Citicoline Sodium (CDP-Choline), Investigator's Brochure," revised Apr. 1994.

Iosifescu et al., "Brain Bioenergetics and Response to Triiodothyronine Augmentation in Major Depressive Disorder," *Biol. Psychiatry* 63:1127-1134, 2008.

Jacobs et al., "Cocaine Abuse: Neurovascular Complications," *Radiology* 170:223-227, 1989.

Jensen et al., "Triacetyluridine (TAU) Decreases Depressive Symptoms and Increases Brain pH in Bipolar Patients," *Exp. Clin. Psychopharmacol.* 16:199-206, 2008.

Jørgensen et al., "Herpes Simplex Virus (HSV) Antibodies in Child Psychiatric Patients and Normal Children," *Acta Psychiatr. Scand.* 66:42-49, 1982.

Karkishchenko et al., "Biosynthesis of Endogenous Pyrimidines in Anxiety and Depressive States of Different Etiologies," *Zh. Nevropatol. Psikhiatr. Im. S. S. Korsakova (J. Neuropath. Psych.)* 91:73-74, 1991.

Katzung, "Basic & Clinical Pharmacolgy," *Appleton & Lang Seventh Edition*, pp. 62 and 521-523, 1998.

Kaufman et al., "Cocaine-Induced Cerebral Vasoconstriction Detected in Humans With Magnetic Resonance Angiography," *JAMA* 279:376-380, 1998.

Kaufman et al., "Cerebral Phosphorus Metabolite Abnormalities in Opiate-Dependent Polydrug Abusers in Methadone Maintenance," *Psychiatry Res.* 90:143-152, 1999.

Kennedy et al., "The Function of Cytidine Coenzymes in the Biosynthesis of Phospholipides," *J. Biol. Chem.* 222:193-214, 1956.

Kimura et al., "N3-Phenacyluridine, a Novel Hypnotic Compound, Interacts with the Benzodiazepine Receptor," *Eur. J. Pharmacol.* 311:265-269, 1996.

Kimura et al., "Possible Existence of a Novel Receptor for Uridine Analogues in the Central Nervous System Using Two Isomers, N3-(S)-(+)- and N3-(R)-(−)-Alpha-Hydroxy-Beta-Phenethyluridines," *Biol. Pharm. Bull.* 24:729-731, 2001.

Kimura et al., "Uridine Receptor: Discovery and Its Involvement in Sleep Mechanism," *Sleep* 24:251-260, 2001.

Konradi et al., "Molecular Evidence for Mitrochondrial Dysfunction in Bipolar Disorder," *Arch. Gen. Psychiatry* 61:300-308, 2004. Correction reprinted in *Arch. Gen. Psychiatry* 61:538, 2004.

Koob et al., "Drug Addiction, Dysregulation of Reward, and Allostasis," *Neuropsychopharmacology* 24:97-129, 2001.

Kouri et al., "Changes in Aggressive Behavior During Withdrawal from Long-Term Marijuana Use," *Psychopharmacology* 143:302-308, 1999.

Kozai et al., "Synthesis and Hypnotic Activities of 4-Thio Analogues of N3-Substituted Uridines," *Chem. Pharm. Bull.* (Tokyo) 49:1185-1188, 2001.

Kreek, "Opiate and Cocaine Addictions: Challenge for Pharmacotherapies," *Pharmacol. Biochem. Behav.* 57:551-569, 1997.

Krooth et al., "Effects of Natural Pyrimidines and of Certain Related Compounds on the Spontaneous Activity of the Mouse," *J. Pharmacol. Exp. Ther.* 207:504-514, 1978.

Levin et al., "Improved Regional Cerebral Blood Flow in Chronic Cocaine Polydrug Users Treated with Buprenorphine," *J. Nucl. Med.* 36:1211-1215, 1995.

London et al., "Cerebral Glucose Utilization in Human Heroin Addicts: Case Reports from a Positron Emission Tomographic Study," *Res. Commun. Subst. Abuse* 10:141-144, 1989.

Lukacsko et al., "Modulation of the Vasoconstrictor Response to Adrenergic Stimulation by Nucleosides and Nucleotides," *J. Pharmocol. Exp. Ther.* 222:344-349, 1982.

Lukas et al., "Effects of Short-Term Citicoline Treatment on Acute Cocaine Intoxication and Cardiovascular Effects," *Psychopharmacology* 157:163-167, 2001.

Lyoo et al., "Multinuclear Magnetic Resonance Spectroscopy of High-Energy Phosphate Metabolites in Human Brain Following Oral Supplementation of Creatine-Monohydrate," *Psychiatry Res.* 123:87-100, 2003.

Lyoo et al., "Frontal Lobe Gray Matter Density Decreases in Bipolar I Disorder," *Biol. Psychiatry* 55:648-651, 2004.

Maas et al., "Functional Magnetic Resonance Imaging of Human Brain Activation During Cue-Induced Cocaine Craving," *Am. J. Psychiatry* 155:124-126, 1998.

Maldonado et al., "Involvement of the Endocannabinoid System in Drug Addiction," *Trends Neurosci.* 29:225-232, 2006.

Malec et al., "Influence of Adenosinergic Drugs on Ethanol Withdrawal Syndrome in Rats," *Pol. J. Pharmacol.* 48:583-588, 1996. (Abstract).

Marangell et al., "A Double-Blind, Placebo-Controlled Study of the Omega-3 Fatty Acid Docosahexaenoic Acid in the Treatment of Major Depression," *Am. J. Psychiatry* 160:996-998, 2003.

Martin et al. "Omega-3 Polyunsaturated Fatty Acids Increase Purine but Not Pyrimidine Transport in L1210 Leukaemia Cells," *Biochem. J.* 315:329-333, 1996.

Martinet et al., "Interaction of CDP-Choline with Synaptosomal Transport of Biogenic Amines and Their Precursors In Vitro and In Vivo in the Rat Corpus Striatum," *Experientia* 34:1197-1199, 1978.

Martinet et al., "Effects of Cytidine-5'-Diphosphocholine on Norepinephrine, Dopamine, and Serotonin Synthesis in Various Regions of the Rat Brain," *Arch. Int. Pharmacodyn.* 239:52-61, 1979.

McCance, "Overview of Potential Treatment Medications for Cocaine Dependence," *NIDA Res. Monogr.* 175:36-72, 1997.

Mezinskis et al., "The Measurement of Craving," *J. Addict. Dis.* 20:67-85, 2001.

Moglia et al., "Citicoline in Patients with Chronic Cerebrovascular Diseases (CCVD): Quantitative EEG Study," *Curr. Ther. Res.* 36:309-313, 1984.

Monti et al., "Adenosine Analogues Modulate the Incidence of Sleep Apnea in Rats," *Pharmacol. Biochem. Behav.* 51:125-131, 1995.

Monticone et al., "On the Therapeutic Use of Nucleosides, Cytidine and Uridine, in Some Neurological Diseases," *Minerva Med.* 57:4348-4352, 1966.

Moore et al., "Lower Levels of Nucleoside Triphosphate in the Basal Ganglia of Depressed Subjects: A Phosphorous-31 Magnetic Resonance Spectroscopy Study," *Am. J. Psychiatry* 154:116-118, 1997.

National Institutes of Health, "Problem Sleepiness," *NIH Publication No. 97-4071*, pp. 1-4, Bethesda, MD, 1997.

Naydenov et al., "Differences in Lymphocyte Electron Transport Gene Expression Levels Between Subjects with Bipolar Disorder and Normal Controls in Response to Glucose Deprivation Stress," *Arch. Gen. Psychiatry* 64:555-564, E1-E7, 2007.

Nicolson et al., "Evidence for Mycoplasma ssp., Chlamydia pneunomiae, and Human Herpes Virus-6 Coinfections in the Blood of Patients with Autistic Spectrum Disorders," *J. Neurosci. Res.* 85:1143-1148, 2007.

O'Leary et al., "Acute Marijuana Effects on rCBF and Cognition: A PET Study," *Neuroreport* 11:3835-3841, 2000.

O'Rourke et al., "Effect of Chronic Cocaine Exposure on Carotid Artery Reactivity in Neonatal Rabbits," *Life Sci.* 59:119-130, 1996.

Orsulak et al., "Antidepressant Drugs: Additional Clinical Uses," *J. Fam. Pract.* 28:209-216, 1989.

Page et al. "Developmental Disorder Associated with Increased Cellular Nucleotidase Activity," *Proc. Natl. Acad. Sci. USA*. 94:11601-11606, 1997.

Pekkanen, "Your Inner Clock," *Washingtonian* 42:131-134, 2007.

Peterson et al., "Neurovascular Complications of Cocaine Abuse," *J. Neuropsychiatry Clin. Neurosci.* 3:143-149, 1991.

Petkov et al., "Effects of the Nootropic Agents Adafenoxate, Meclofenoxate and the Acetylcholine Precursor Citicholine on the Brain Muscarinic Receptors (Experiments on Rats)," *Acta Physiol. Pharmacol. Bulg.* 13:3-10, 1987.

Petkov et al., "Changes in the Brain Biogenic Monoamines Induced by the Nootropic Drugs Adafenoxate and Meclofenoxate and by Citicholine (Experiments on Rats)," *Gen. Pharmacol.* 21:71-75, 1990.

Pleul et al., "Lithium Therapy and the Turnover of Phosphatidylcholine in Human Erythrocytes," *Eur. J. Clin. Pharmacol.* 31:457-462, 1986.

Pokrovsky, "Encyclopedic Dictionary of Medical Terms," *Meditsina Publishers* (Moscow), pp. 97, 265, 2001.

Pugh et al., "Stedman's Medical Dictionary," *Lippincott Williams & Wilkins, 27th Edition*, Entry for "Insomnia," pp. 906-907, 2000.

Purdue News, "Deficiency in Omega-3 Fatty Acids Tied to ADHD in Boys," Jun. 1996.

Radulovacki et al., "Adenosine Analogs and Sleep in Rats," *J. Pharmacol. Exp. Ther.* 228:268-274, 1984.

Regenold et al., "Cerebrospinal Fluid Evidence of Increased Extra-Mitochondrial Glucose Metabolism Implicates Mitochondrial Dysfunction in Multlple Sclerosis Disease Progression," *J. Neurol. Sci.* 275:106-112, 2008.

Regenold et al., "Elevated Cerebrospinal Fluid Lactate Concentrations in Patients with Bipolar Disorder and Schizophrenia: Implications for the Mitochondrial Dysfunction Hypothesis," *Biol. Psychiatry* 65:489-494, 2009.

Rejdak et al., "Citicoline Treatment Increases Retinal Dopamine Content in Rabbits," *Ophthalmic Res.* 34:146-149, 2002.

Renshaw et al., "Basal Ganglia Choline Levels in Depression and Response to Fluoxetine Treatment: An In Vivo Proton Magnetic Resonance Spectroscopy Study," *Biol. Psychiatry* 41:837-843, 1997.

Renshaw et al., "Short-Term Treatment with Citicoline (CDP-Choline) Attenuates Some Measures of Craving in Cocaine-Dependent Subjects: A Preliminary Report," *Psychopharmacology* 142:132-138, 1999.

Renshaw et al., "Multinuclear Magnetic Resonance Spectroscopy Studies of Brain Purines in Major Depression," *Am. J. Psychiatry* 158:2048-2055, 2001.

Repligen Press Release, "Repligen Reports Third Quarter 2001 Results: Company Updates Progress on Product Development Programs," pp. 1-2, Feb. 1, 2001.

Repligen Press Release, "Repligen Reports Phase 1 Results of RG2133 in Bipolar Disorder and Depression: Additional Studies Planned with Uridine in Bipolar Disorder," pp. 1-2, Jun. 9, 2004.

Repligen Press Release, "Repligen Reports Phase 1 Results of RG2133 in Bipolar Disorder and Depression: Additional Studies Planned with Uridine in Bipolar Disorder," pp. 1-2, Jun. 10, 2004.

Repligen Press Release, "Repligen's RG2417 Demonstrates Positive Activity in Preclinical Model of Anxiety: Data Presented at the Annual Meeting of Society for Neuroscience," pp. 1-2, Oct. 25, 2004.

Repligen Press Release, "Repligen Reports Initial Clinical Data for Secretin in Schizophrenia: Follow-on Study Planned to Target a Cognitive Deficit of Schizophrenia," pp. 1-2, Feb. 4, 2005.

Richardson et al., "Laterality Changes Accompanying Symptom Remission in Schizophrenia Following Treatment with Eicosapentaenoic Acid," *Int. J. Psychophysiol.* 34:333-339, 1999.

Roitman et al., "Creatine Monohydrate in Resistant Depression: A Preliminary Study," *Biopolar. Disord.* 9:754-758, 2007.

Romanov, "Sleep Medicine," *Slovo Publishers* (Moscow), p. 69, 1998.

Saligaut et al., "Capture de Dopamine Striatale Chez le Rat: Effects d'une Hypoxie Hypobare Agiüe et/ou d'un Traitement Oral Par la Cytidine Diphosphocholine" *Circulation et Métabolisme du Cerveau* 2:33-42, 1984. (English Abstract).

Saligaut et al., "Circling Behaviour in Rats with Unilateral Lesions of the Nigrostriatum Induced by 6—Hydroxydopamine: Changes Induced by Oral Administration of Cytidine-5'- Diphosphocholine," *Neuropharmacology* 26:1315-1319, 1987.

Saligaut et al., "Effects of Hypoxia and Cytidine (5') Diphosphocholine on the Concentrations of Dopamine, Norepinephrine and Metabolites in Rat Hypothalamus and Striatum," *Arch. Int. Pharmacodyn. Ther.* 285:25-33, 1987.

Salvadorini et al., "Clinical Evaluation of CDP-Choline (NICHOLIN®): Efficacy as Antidepressant Treatment," *Curr. Ther. Res. Clin. Exp.* 18:513-520, 1975.

Satoh et al., "Involvement of Adenosine $A_{2A}$ Receptor in Sleep Promotion," *Eur. J. Pharmacol.* 351:155-162, 1998.

Scammell et al., "An Adenosine A2a Agonist Increases Sleep and Induces Fos in Ventrolateral Preoptic Neurons," *Neuroscience* 107:653-663, 2001.

Schloesser et al., "Cellular Plasticity Cascades in the Pathophysiology and Treatment of Bipolar Disorder," *Neuropsychopharmacology* 33:110-133, 2008.

Secades et al., "CDP-Choline: Pharmacological and Clinical Review," *Methods Find. Exp. Clin. Pharmacol.* 17(Suppl. B):1-54, 1995. (Abstract).

Self et al., "Opposite Modulation of Cocaine-Seeking Behavior by $D_1$- and $D_2$-Like Dopamine Receptor Agonists," *Science* 271:1586-1589, 1996.

Shargel et al., "Comprehensive Pharmacy Review," *Lippincott Williams & Wilkins, Fourth Edition*, pp. 547-548, 2001.

Sharpe, "CDP-Choline and Alpha-GPC: What to Feed Your Head," http://www.delano.com/ReferenceArticles/CDPc-aGPC-Sharpe. html, Feb. 15, 2006, pp. 1-6.

Shekim et al., "S-Adenosyl-L-Methionine (SAM) in Adults with ADHD, RS: Preliminary Results from an Open Trial," *Psychopharmacol. Bull.* 26:249-253, 1990.

Shibuya et al., "Effects of CDP-Choline on Striatal Dopamine Levels and Behavior in Rats," *Jpn. J. Pharmacol.* 31:47-52, 1981.

Sholar et al., "Concurrent Pharmacokinetic Analysis of Plasma Cocaine and Adrenocorticotropic Hormone in Men," *J. Clin. Endocrinol. Metab.* 83:966-968, 1998.

Silveri et al., "S-Adenosyl-L-Methionine: Effects on Brain Bioenergetic Status and Transverse Relaxation Time in Healthy Subjects," *Biol. Psychiatry* 54:833-839, 2003.

Silveri et al., "Oral Citicoline Supplementation Significantly Alters Phosphorus Metabolites in the Anterior Cingulate Cortex," Program No. 301.2, Poster No. VV16, 2007 Neuroscience Meeting Planner. San Diego, CA: Society for Neuroscience, Nov. 4, 2007. (Abstract).

Silveri et al., "Citicoline Enhances Frontal Lobe Bioenergetics as Measured by Phosphorus Magnetic Resonance Spectroscopy," *NMR Biomed.* 21:1066-1075, 2008.

Spielman et al., "Treatment of Chronic Insomnia by Restriction of Time in Bed," *Sleep* 10:45-56, 1987.

Stoll et al., "Choline in the Treatment of Rapid-Cycling Bipolar Disorder: Clinical and Neurochemical Findings in Lithium-Treated Patients," *Biol. Psychiatry* 40:382-388, 1996.

Stoll et al., "Omega 3 Fatty Acids in Bipolar Disorder: a Preliminary Double-Blind, Placebo-Controlled Trial," *Arch. Gen. Psychiatry* 56:407-412, 1999.

Stork et al., "Mitochondrial Dysfunction in Bipolar Disorder: Evidence from Magnetic Resonance Spectroscopy Research," *Mol. Psychiatry* 10:900-919, 2005.

Stradomskii et al., "Pyrimidine Metabolism in Depression Anxiety Disorders," *Izvestiya Severo-Kavkazskogo Nauchnogo Tsentra Vysshei Shkoly Estestvennye Nauki* 1:106-110, 1990. (Abstract).

Sun et al. "Observation of Therapeutic Effects of High Dose Citicoline on the Emergency Treatment of 100 Cases of Hypnotics Poisoning," *China Pharmacist* 2:77-78, 1999. (English translation, pp. 1-3).

Tanskanen et al., "Fish Consumption and Depressive Symptoms in the General Population in Finland," *Psychiatr. Serv.* 52:529-531, 2001.

Tazaki et al., "Treatment of Acute Cerebral Infarction with a Choline Precursor in a Multicenter Double-Blind Placebo-Controlled Study," *Stroke* 19:211-216, 1988.

Teicher et al., "Functional Deficits in Basal Ganglia of Children with Attention-Deficit/Hyperactivity Disorder Shown with Functional Magnetic Resonance Imaging Relaxometry," *Nat. Med.* 6:470-473, 2000.

Teoh et al., "Acute Interactions of Buprenorphine with Intravenous Cocaine and Morphine: An Investigational New Drug Phase I Safety Evaluation," *J. Clin. Psychopharmacol.* 13:87-99, 1993.

Tornos et al., "Effect of Oral CDP-Choline on Experimental Withdrawal Syndrome," *Arzneim.-Forsch.* 33:1018-1021, 1983.

Trovarelli et al., "The Influence of Cytidine on the Endogenous Pool of CDP-Choline, CDP-Ethanolamine, and CMP of the Rat Brain," *Neurochem. Res.* 9:73-79, 1984.

Tucker et al. "Inhibition by Adenosine Analogs of Opiate Withdrawal Effects," *NIDA Res. Monogr.* 49:85-91, 1984.

U.S. Surgeon General, "Overview of ADHD and its Treatments" *U.S. Office of the Surgeon General, Mental Health Matters*, pp. 1-6, 2000-2001.

van Groeningen et al., "Clinical and Pharmacokinetic Studies of Prolonged Administration of High-Dose Uridine Intended for Rescue from 5-FU Toxicity," *Cancer Treat. Rep.* 70:745-750, 1986.

van Groeningen et al., "Clinical and Pharmacologic Study of Orally Administered Uridine," *J. Natl. Cancer Inst.* 83:437-441, 1991.

Virtue, "Nutrition as Attention Deficit Disorder ADHD Alternative Treatment: Help is as Close as the Kitchen," www.naturalhealthweb.com 1999. (last accessed Oct. 29, 2009).

Warner et al., "Pharmacotherapy for Opioid and Cocaine Abuse," *Med. Clin. North Am.* 81:909-925, 1997.

Weiss, "Metabolism and Actions of CDP-Choline as an Endogenous Compound and Administered Exogenously as Citicoline," *Life Sci.* 56:637-660, 1995.

Wilson, "Increasing Serotonin Crucial for Treating Obsessive-Compulsive Disorder: Presented at SFN," *Doctor's Guide Personal Edition*, pp. 1-2, Nov. 14, 2003.

Wurtman et al., "Effect of Oral CDP-Choline on Plasma Choline and Uridine Levels in Humans," *Biochem. Pharmacol.* 60:989-992, 2000.

Wurtman et al., "Synaptic Proteins and Phospholipids are Increased in Gerbil Brain by Administering Uridine Plus Docosahexaenoic Acid Orally," *Brain Res.* 1088:83-92, 2006.

Wurtman et al., "Synapse Formation is Enhanced by Oral Administration of Uridine and DHA, the Circulating Precursors of Brain Phosphatides," *J. Nutr. Health Aging* 13:189-197, 2009.

Yoon et al., "Decreased Glutamate/Glutamine Levels May Mediate Cytidine's Efficacy in Treating Bipolar Depression: A Longitudinal Proton Magnetic Resonance Spectroscopy Study," *Neurophyschopharmacology* 34:1810-1818, 2009.

Zaharov et al., "Cognitive Disorders in Neurology Practice," *A Difficult Patient* No. 5, 2005. [Available at http://www.t-pacient.ru/archive/n5-2005/n5-2005_23.html].

Zhao et al., "Effects of Uridine in Models of Epileptogenesis and Seizures," *Epilepsy Res.* 70:73-82, 2006.

Zhao et al., "Effects of Uridine on Kindling," *Epilepsy Behav.* 13:47-51, 2008.

International Search Report and Written Opinion for PCT/US05/28407 (mailed Dec. 30, 2005).

Extended European Search Report and Communication for EP05784282.5 (mailed May 25, 2010).

English Translation of Official Action from the Patent Office of the Russian Federation for Application No. 2005122934/14 (issued Jun. 12, 2009).

Reply to Office Action and Declaration of Dr. James Rusche, submitted in U.S. Appl. No. 11/629,111 on Feb. 22, 2010.

Baldessarini et al., "Suicide Risk and Treatments for Patients with Bipolar Disorder," *JAMA* 290:1517-1519, 2003.

IMSDRUGNEWS Database Entry, Accession No. 2003:368, "Triacetyluridine: Repligen Phase Change II, USA (Bipolar Disease)," p. 1, Feb. 3, 2003.

Mealy et al., "RG-2133," *Drugs of the Future* 29:969, 2004.

McLean Hospital Press Release, "Repligen Announces Initiation of Clinical Trial of Uridine: McLean Hospital Study Will Assess Changes in Brain Chemistry in Bipolar and Major Depression," pp. 1-2, Jan. 23, 2003.

Saydoff et al., "Oral Uridine Pro-Drug PN401 Decreases Neurodegeneration, Behavioral Impairment, Weight Loss and Mortality in the 3-Nitropropionic Acid Mitochondrial Toxin Model of Huntington's Disease," *Brain Res.* 994:44-54, 2003.

U.S. Department of Health and Human Services, "The Health Consequences of Smoking: Nicotine Addiction (a report of the Surgeon General, 1988)," 1988 (643 pages).

\* cited by examiner

COMPOUNDS FOR THE TREATMENT OF MARIHUANA DEPENDENCE, WITHDRAWAL, AND USAGE

BACKGROUND OF THE INVENTION

This invention relates to methods for the treatment or suppression of marihuana dependence, withdrawal, or usage.

Substance abuse disorders present unique complications for patients, clinicians, and care givers. These disorders are difficult to diagnose unequivocally and fear of societal condemnation, as well as lack of simple and effective therapies, often results in patients who are reluctant to disclose their symptoms to health professionals, leading to adverse societal and health consequences. Substance abuse disorders, e.g., marihuana usage or dependence, occur in people of all ages and backgrounds.

Use of substances such as marihuana often leads to addiction and dependence on these substances, causing a variety of adverse consequences, including clinical toxicity, residual neuropsychological impairment, memory loss, physical dependence and withdrawal symptoms, and an impaired ability to maintain social and professional relationships. In addition, marihuana is the most widely abused illicit drug in the world. The etiology of substance abuse or dependence is unknown, although factors such as the user's physical characteristics (e.g., genetic predisposition, age, weight), personality, or socioeconomic class have been postulated to be determinants.

Simple and effective pharmacological treatments for these disorders have proven scarce to date. It would be beneficial to provide pharmacotherapies suitable for administration to all populations, including children and pregnant women, for the treatment of marihuana dependence, withdrawal, or usage.

SUMMARY OF THE INVENTION

In general, the invention features methods of treating or suppressing marihuana dependence, withdrawal, or usage by administering a therapeutically-effective amount of a cytidine-containing, cytosine-containing, creatine-containing, uridine-containing, adenosine-containing, or adenosine-elevating compound to a mammal. Any of the cytidine-containing, cytosine-containing, creatine-containing, uridine-containing, adenosine-containing, or adenosine-elevating compounds of the invention may be administered separately or in combination.

Specific effects of dependence, withdrawal, or usage that may be treated by the methods described herein include psychomotor performance deficits, memory loss, sleep disorders, decreased appetite, emotional symptoms (e.g., increased aggression, anger, anxiety, irritability, nervousness, or restlessness), physical symptoms (e.g., tension, headache, hot flashes, nausea, chills, or sweating), and craving (e.g., caused by withdrawal, drug exposure, stress, or cues). The methods may also be used for primary or secondary treatment of neurobiological damage associated with chronic marihuana use, e.g., general memory deficits and impairment in learning, retention, and retrieval.

In preferred embodiments, the cytidine-containing compound is cytidine or CDP. The cytidine-containing compound may include choline, e.g., CDP-choline. The uridine-containing compound is, for example, uridine, UMP, UDP, UTP, or triacetyl uridine. The mammal is, for example, a human child (e.g., born to a dependent mother), adolescent, adult (e.g., a pregnant woman), or older adult. In other preferred embodiments, the CDP-choline is administered orally and the administration is chronic, e.g., treatment occurring over a period of greater than 1, 2, 3, 4, 5, 6, 7, 14, 21, 30, 60, 90, or 180 days or even over a period of greater than one year. In one embodiment, treatment of marihuana withdrawal occurs over at least 10 days, e.g., for one month.

The method may also include diagnosing the mammal with marihuana dependence, withdrawal, or usage prior to administration of a therapeutic compound. In addition, the mammal may remain under the care of a physician during treatment. Treatment may further include psychological intervention, such as cognitive behavioral therapy for treating insomnia or Group Drug Counseling.

The methods of the invention may treat or suppress marijuana dependence, withdrawal, or usage in a mammal that may or may not have a co-morbid condition. Such co-morbid conditions include co-morbid drug use or dependence, e.g., from alcohol, nicotine, cocaine, opiates, or caffeine; neurological or psychiatric conditions, e.g., depression, dysthymia, and attention-deficit hyperactivity disorder; sleep disorders, e.g., insomnia, constructive or obstructive sleep apnea, restless leg syndrome, periodic limb movements, problem sleepiness, or narcolepsy; or a physical condition. The methods of the invention may also be employed on mammals that are otherwise physically and/or mentally healthy.

In other preferred embodiments, a brain phospholipid (e.g., lecithin) or a brain phospholipid precursor (e.g., a fatty acid or a lipid) is also administered to the mammal. An antidepressant may also be administered to the mammal.

By use of "marihuana" is meant use of any form of marihuana including cigarettes and brownies. The term also encompasses formulations including a tetrahydrocannabinol (e.g., $\Delta^1$-3,4-trans isomer or $\Delta^6$-3,4-trans isomer), the active ingredients in marihuana.

By "abuse" is meant excessive use of a substance, particularly one that may modify body functions.

By "dependence" or "dependency" is meant any form of behavior that indicates an altered or reduced ability to make decisions resulting, at least in part, from the use of marihuana. Representative forms of dependency behavior may take the form of antisocial, or inappropriate behavior and include those behaviors directed at the desire, planning, acquiring, and use of marihuana. This term also includes the psychic craving for marihuana that may or may not be accompanied by a physiological dependency, as well as a state in which there is a compulsion to use marihuana, either continuously or periodically, in order to experience its psychic effects or to avoid the discomfort of its absence. Forms of dependency include habituation, that is, an emotional or psychological dependence on marihuana to obtain relief from tension and emotional discomfort; tolerance, that is, the progressive need for increasing doses to achieve and sustain a desired effect; addiction, that is, physical or physiological dependence which is beyond voluntary control; and use of marihuana to prevent withdrawal symptoms. Dependency may be influenced by a number of factors, including physical characteristics of the user (e.g., genetic predisposition, age, gender, or weight), personality, or socioeconomic class.

By marihuana "usage" is meant the intake of marihuana by any route. The term also includes marihuana abuse.

By "treating" is meant the medical management of a patient with the intent that a cure, amelioration, or prevention of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; preventive treatment, that is, treatment directed to prevention of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

By "suppressing" is meant reducing the desire, need, or number of usages of marihuana.

By "therapeutically-effective amount" is meant an amount of a cytidine-containing, cytosine-containing compound, a uridine-containing compound, a creatine-containing compound, an adenosine-containing compound, and an adenosine-elevating compound sufficient to produce a healing, curative, prophylactic, stabilizing, preventative, or ameliorative effect in the treatment or suppression of marihuana usage, withdrawal, or dependence.

By "cytidine-containing compound" is meant any compound that includes, as a component, cytidine, CMP, CDP, CTP, dCMP, dCDP, or dCTP. Cytidine-containing compounds can include analogs of cytidine. Preferred cytidine-containing compounds include, without limitation, CDP-choline and cytidine 5'-diphosphocholine, frequently prepared as cytidine 5'-diphosphocholine [sodium salt] and also known as citicoline.

By "cytosine-containing compound" is meant any compound that includes, as a component, cytosine. Cytosine-containing compounds can include analogs of cytosine.

By "adenosine-containing compound" is meant any compound that includes, as a component, adenosine. Adenosine-containing compounds can include analogs of adenosine.

By "adenosine-elevating compound" is meant any compound that elevates brain adenosine levels, for example, compounds which inhibit or alter adenosine transport or metabolism (e.g., dipyridamole or S-adenosylmethionine).

By "uridine-containing compound" is meant any compound that includes as a component uridine or UTP. Uridine-containing compounds can include analogs of uridine. Exemplary uridine-containing compounds include uridine, orotic acid, mono-, di- or tri-esters of uridine, including mono-, di-, and triacetyl uridine, and mono, di- or tri-phosphates of uridine including UMP, UDP, and UTP.

By "creatine-containing compound" is meant any compound that includes as a component, creatine. Creatine-containing compounds can include analogs of creatine.

By "phospholipid" is meant a lipid containing phosphorus, e.g., phosphatidic acids (e.g., lecithin), phosphoglycerides, sphingomyelin, and plasmalogens. By "phospholipid precursor" is meant a substance that is built into a phospholipid during synthesis of the phospholipid, e.g., fatty acids, glycerol, or sphingosine.

By "child or adolescent" is meant an individual who has not attained complete growth and maturity. Generally, a child or adolescent is under twenty-one years of age.

By "older adult" is meant an individual who is in the later stage of life. Generally, an older adult is over sixty years of age.

The compounds utilized herein are relatively non-toxic, and CDP-choline, uridine, and triacetyl uridine, in particular, are pharmacokinetically understood and known to be well tolerated by mammals. The present invention, therefore, provides treatments that are likely to have few adverse effects and may be administered to children and adolescents, as well as the elderly, or those whose health is compromised because of existing physical conditions.

Other features and advantages will be apparent from the following description and the claims.

DETAILED DESCRIPTION OF THE INVENTION

The invention described herein features methods for the treatment or suppression of marihuana dependence, withdrawal, or usage.

To this end, the invention features the use of cytidine-containing, cytosine-containing, uridine-containing, creatine-containing, adenosine-containing, and adenosine-elevating compounds to alleviate symptoms of these disorders. A preferred cytidine-containing compound is CDP-choline (also referred to as citicoline or CDP choline [sodium salt]), a preferred adenosine-containing compound is S-adenosylmethionine (SAMe), and a preferred uridine-containing compound is triacetyl uridine. Compounds useful in the methods described herein also include encapsulated compounds, e.g., liposome- or polymer-encapsulated cytidine-containing, cytosine-containing, uridine-containing, creatine-containing, adenosine-containing, and adenosine-elevating compounds. Useful compounds further include those linked (e.g., covalently or non-covalently) to various antibodies, ligands, or other targeting and enveloping or shielding agents (e.g., albumin or dextrose), to allow the cytidine-containing, cytosine-containing, uridine-containing, creatine-containing, adenosine-containing, or adenosine-elevating compound to reach the target site (e.g., the central nervous system) prior to being removed from the blood stream, e.g., by the kidneys and liver, and prior to being degraded.

The cytidine-containing, cytosine-containing, uridine-containing, creatine-containing, adenosine-containing, or adenosine-elevating compounds may also be co-administered with other compounds that are precursors for the synthesis of brain phospholipids, e.g., fatty acids, lipids, or lecithin.

Marihuana Usage, Withdrawal, or Dependence

Figure 1:
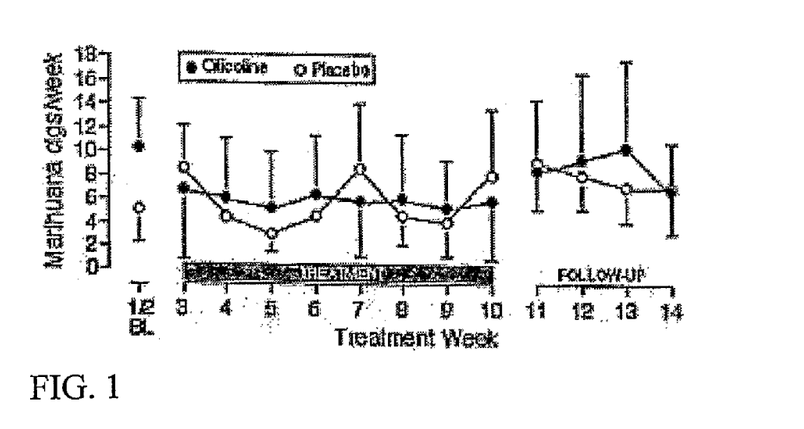
FIG. 1 is a graph of a time course of weekly marihuana use in citicoline- and placebo-treated cocaine-dependent subjects. Subjects were treated with either citicoline or placebo for 8 weeks and then asked to keep track of their drug use patterns via a daily diary. Follow up weeks were conducted under a no drug condition.

Surprisingly, we have discovered that CDP-choline is useful for the treatment of marihuana dependence, withdrawal, or usage, and believe that other, related compounds may be similarly useful. FIG. 1 shows data collected from daily diaries that marihuana use in the subjects typically ranged from 5-10 cigarettes per week. Compared to placebo treatment, marihuana use was reduced during citicoline treatment (weeks 3-10) as reported using the daily diaries. Marihuana use during placebo treatment, while variable, did not decline below baseline levels. There is a group difference at baseline; this difference occurred because subjects were not matched for marihuana use in this study, and these subjects were not dependent on cannabis. Despite this difference, these data revealed an effect on marihuana intake between treatment with citicoline and placebo.

Figure 2:
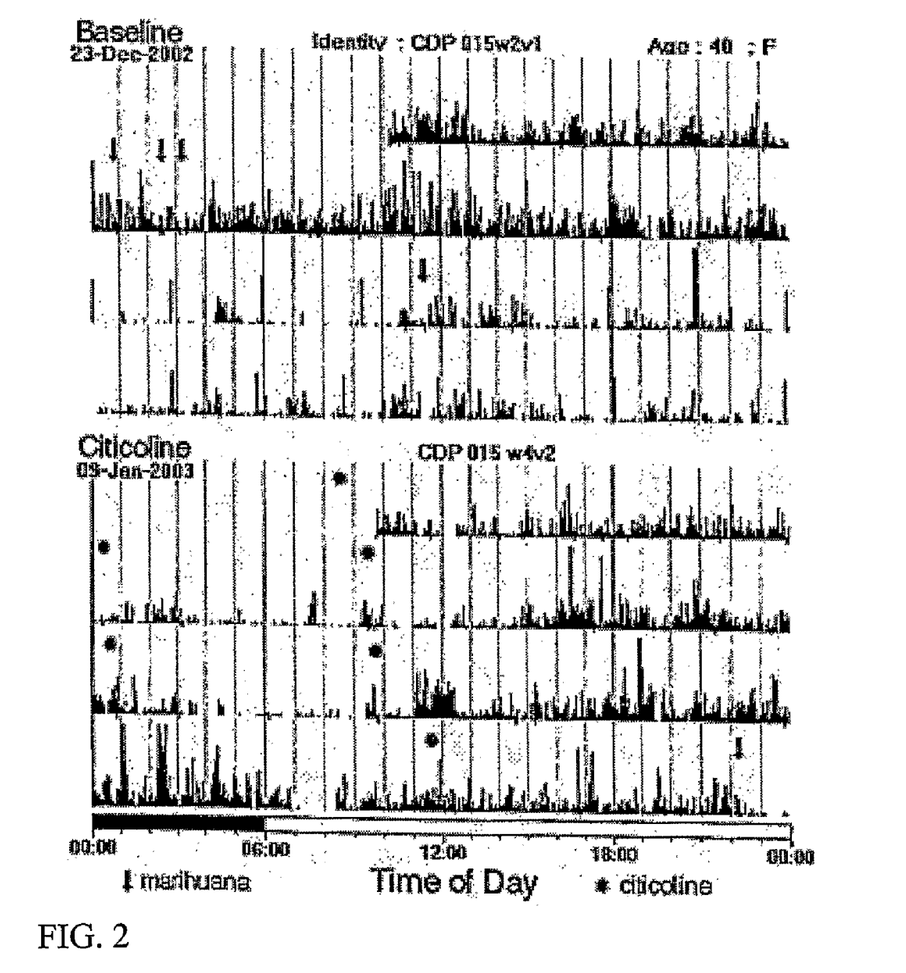
FIG. 2 is a graph of activity of a representative cocaine dependent person two weeks prior to (Baseline) and two weeks after (Citicoline) treatment with citicoline. The graph shows a detailed distribution of sleep wake activity (vertical black lines), marihuana use (arrows), and citicoline treatment (dots) in a representative subject. Marihuana cigarettes are depicted by the arrows. Each strip recording is a 24 hour period of consecutive days. Activity was determined by use of an accelerometer worn on the subject's wrist (ActiWatch Score).

Data in FIG. 2 also show a decrease in the number of marihuana cigarettes smoked and a more normalized, diurnal sleep pattern after treatment with citicoline. Subjects were given either placebo or 500 mg, twice daily of citicoline. This subject, and other cocaine-dependent subjects, displayed a disrupted degree of physical activity, as seen by a low amplitude of the accelerometer (vertical lines), during active drug use typical of the baseline period (Baseline, top 5 tracings). The subject's binge use of marihuana (arrows on second day) is clearly defined. The bottom 4 tracings of FIG. 2 show the same subject on days 10-14 of citicoline treatment. In addition to the reduced marihuana use, citicoline impacted the subject's sleep wake profile—the subject developed a more normalized diurnal pattern of sleeping at night and became more active during the day. This pattern continued throughout the 8 weeks of treatment for this subject.

The success of treatment may be monitored by methods known in the art, e.g., analytical methods (e.g., blood or urine tests), objective measures of sleep activity (e.g., from a wrist actigraphy device (ActiWatch); see also U.S. application Ser. No. 10/740,075), daily diaries, patient interview (e.g., via the Addictive Severity Index) and self evaluation (e.g., patients may evaluate the severity of symptoms on a numerical scale), and neurological function tests (such as Wisconsin Card Sorting, Trail Making Part B, Block Design, Digit Symbol Substitution Test (DSST), Digit Span, and Stroop).

Use of marihuana, especially chronic use or abuse, may result in symptoms such a psychomotor performance deficits, memory loss, sleep disorders, reduced cognitive performance, reduced selective attention, and neurobiological damage (such as general memory deficits and impairment in learning, retention, and retrieval).

Symptoms of marihuana withdrawal include increases in drug craving, decreased appetite, difficulty sleeping, memory loss, psychomotor performance deficits, emotional symptoms (such as increased anger, aggression, restlessness, nervousness, anxiety, irritability, and tension), and physical symptoms (such as headache, hot flashes, nausea, chills, and sweating) (Budney et al. Arch Gen Psychiatry 2001, 58:917). Symptoms of withdrawal are typically most pronounced in the first ten days, e.g., 1-7 days, after cessation of marihuana use. Treatment of withdrawal can be monitored by methods known in the art, e.g., by monitoring a Global Symptom Severity index (Kouri et al. Psychopharmacology 1999, 143: 302; Kouri et al. Exp Clin Psychopharmacol 2000, 8:483-492).

Marihuana craving may be a substantial factor in a subject's inability to reduce marihuana usage. Craving may occur through several mechanisms, e.g., withdrawal-related craving, cue-triggered craving (craving caused by reminders of past drug use), drug exposure triggered craving, and stress-triggered craving. End points for treating craving include preventing craving, reducing craving, and preventing drug use in the presence of craving. Craving may be measured by methods known in the art, such as a questionnaire (Heishman et al. Addiction 2001, 96:1023).

Cytidine-Containing and Cytosine-Containing Compounds

Useful cytidine-containing or cytosine-containing compounds may include any compound comprising one of the following: cytosine, cytidine, CMP, CDP, CTP, dCMP, dCDP, and dCTP. Preferred cytidine-containing compounds include CDP-choline and cytidine 5'-diphosphocholine [sodium salt]. This list of cytidine-containing and cytosine-containing compounds is provided to illustrate, rather than to limit the invention, and the compounds described above are commercially available, for example, from Sigma Chemical Company (St. Louis, Mo.).

CDP-choline is a naturally occurring compound that is hydrolyzed into its components of cytidine and choline in vivo. CDP-choline is synthesized from cytidine-5'-triphosphate and phosphocholine with accompanying production of inorganic pyrophosphate in a reversible reaction catalyzed by the enzyme CTP:phosphocholine cytidylyltransferase (Weiss, Life Sciences 56:637-660, 1995). CDP-choline is available for oral administration in a 500 mg oblong tablet. Each tablet contains 522.5 mg CDP-choline sodium, equivalent to 500 mg of CDP-choline. Matching placebo tablets are also available. Other excipients contained in both active and placebo tablets are talc, magnesium stearate, colloidal silicon dioxide, hydrogenated castor oil, sodium carboxy-methylcellulose, and microcrystalline cellulose.

Other formulations for treatment or suppression of marihuana usage or dependence may take the form of a cytosine-containing or cytidine-containing compound combined with a pharmaceutically-acceptable diluent, carrier, stabilizer, or excipient.

Adenosine-Containing and Adenosine-Elevating Compounds

Adenosine-containing or adenosine-elevating compounds also provide useful therapies. Useful adenosine-containing or adenosine-elevating compounds include, without limitation, any compound comprising one of the following adenosine, ATP, ADP, or AMP. One preferred adenosine-containing compound is S-adenosylmethionine (SAMe).

In addition, compounds are known that are capable of increasing adenosine levels by other mechanisms. For example, adenosine uptake can be inhibited by a number of known compounds, including propentofylline (described in U.S. Pat. No. 5,919,789). Another known compound that inhibits adenosine uptake is EHNA.

Other useful compounds that can be used to increase brain adenosine levels are those that inhibit enzymes that break down adenosine, (e.g., adenosine deaminase and adenosine kinase). Finally, administering compounds that contain adenosine or precursors of adenosine, which are released as adenosine in vivo, can also be used.

Uridine-Containing Compounds

Uridine and uridine-containing compounds provide useful therapies because these compounds can be converted to CTP, a rate-limiting factor in PC biosynthesis (Wurtman et al., Biochemical Pharmacology 60:989-992, 2000). Useful uridine-containing compounds include, without limitation, any compound comprising uridine, UTP, UDP, or UMP. A preferred uridine-containing compound is triacetyl uridine. Uridine and uridine-containing compounds and analogs are well tolerated in humans.

Creatine-Containing Compounds

Creatine and creatine-containing compounds provide useful therapies because these compounds, by virtue of increasing brain phospholipid levels, can raise the levels of ATP. Creatine and creatine-containing compounds are known to be well tolerated at relatively high doses in humans.

Administration

Conventional pharmaceutical practice is employed to provide suitable formulations or compositions for administration to patients. Oral administration is preferred, but any other appropriate route of administration may be employed, for example, parenteral, intravenous, subcutaneous, intramuscular, intracranial, intraorbital, ophthalmic, intraventricular, intracapsular, intraspinal, intracistemal, intraperitoneal, intranasal, or aerosol administration. Therapeutic formulations may be in the form of liquid solutions or suspensions (as, for example, for intravenous administration); for oral administration, formulations may be in the form of liquids, tablets, or capsules; and for intranasal formulations, in the form of powders, nasal drops, or aerosols.

Methods well known in the art for making formulations are described, for example, in "Remington: The Science and Practice of Pharmacy" (20th ed.) ed. A. R. Gennaro, 2000, Lippincott, Philadelphia, Pa. Formulations for parenteral administration may, for example, contain excipients, sterile water, saline, polyalkylene glycols such as polyethylene glycol, oils of vegetable origin, or hydrogenated naphthalenes.

If desired, slow release or extended release delivery systems may be utilized. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Preferably, the compounds of the invention, such as CDP-choline, are administered at a dosage of at least 500 mg, e.g., 1000 or 2000 mg, twice daily by oral administration. Orally administered CDP-choline is bioavailable, with more than 99% of CDP-choline and/or its metabolites absorbed and less than 1% excreted in feces. CDP-choline, administered either orally or intravenously, is rapidly converted into the two major circulating metabolites, choline and cytidine. Major excretion routes are lung (12.9%) and urine (2.4%); the rest of the dose (83.9%) is apparently metabolized and retained in tissues.

In general, the compounds of the invention, such as CDP-choline, uridine, UTP, creatine, or SAMe, are administered at a dosage appropriate to the effect to be achieved and are typically administered in unit dosage form. The dosage preferably ranges from 50 mg per day to 4000 mg per day. The exact dosage of the compound may be dependent, for example, upon the age and weight of the recipient, the route of administration, and the severity and nature of the symptoms to be treated. In general, the dosage selected should be sufficient to treat or suppress marihuana usage or dependence, or one or more symptoms thereof, without producing significant toxic or undesirable side effects. As noted above, the preferred route of administration for most indications is oral.

In the case of CDP-choline, there have been no reported cases of overdoses. CDP-choline toxicity is largely self-limiting, ingestion of large amounts in preclinical studies shows common cholinergic symptoms (salivation, lacrimation, urination, defecation, and vomiting).

Combination with Other Therapies

The cytidine-containing, cytosine-containing, uridine-containing, creatine-containing, adenosine-containing, and adenosine-elevating compounds of the invention may be administered as a monotherapy, in combination with each other, or in combination with other therapies for the treatment of substance abuse disorders, including therapies for the treatment or suppression of marihuana usage, withdrawal, or dependence, or other associated physiological or psychological conditions.

The compounds of the invention, may be administered in conjunction with lower doses of other therapeutic compounds for these disorders, including stimulants and antidepressants. For example, the compounds of the invention may be administered with phospholipids, e.g., lecithin, or with brain phospholipid precursors, e.g., fatty acids or lipids, or may be administered as an adjunct to standard therapy for the treatment of substance abuse disorders.

In one particular example, the compound of the invention may be administered in combination with an antidepressant, anticonvulsant, antianxiety, antimanic, antipyschotic, antiobsessional, sedative-hypnotic, stimulant, or anti-hypertensive medication. Examples of these medications include, but are not limited to, the antianxiety medications, alprazolam, buspirone hydrochloride, chlordiazepoxide, chlordiazepoxide hydrochloride, clorazepate dipotassium, desipramine hydrochloride, diazepam, halazepam, hydroxyzine hydrochloride, hydroxyzine pamoate, lorazepam, meprobamate, oxazepam, prazepam, prochlorperazine maleate, prochlorperazine, prochlorperazine edisylate, and trimipramine maleate; the anticonvulsants, amobarbital, amobarbital sodium, carbamazepine, chlordiazepoxide, chlordiazepoxide hydrochloride, clorazepate dipotassium, diazepam, divalproex sodium, ethosuximide, ethotoin, gabapentin, lamotrigine, magnesium sulfate, mephenytoin, mephobarbital, methsuximide, paramethadione, pentobarbital sodium, phenacemide, phenobarbital, phenobarbital sodium, phensuximide, phenytoin, phenytoin sodium, primidone, secobarbital sodium, trimethadione, valproic acid, and clonazepam; the antidepressants, amitriptyline hydrochloride, amoxapine, bupropion hydrochloride, clomipramine hydrochloride, desipramine hydrochloride, doxepin hydrochloride, fluoxetine, fluvoxamine, imipramine hydrochloride, imipramine pamoate, isocarboxazid, lamotrigine, maprotoline hydrochloride, nortriptyline hydrochloride, paroxetine hydrochloride, phenelzine sulfate, protriptyline hydrochloride, sertraline hydrochloride, tranylcypromine sulfate, trazodone hydrochloride, trimipramine maleate, and venlafaxine hydrochloride; the antimanic medications, lithium carbonate and lithium citrate; the antiobsessional medications, fluvoxamine, and clomipramine hydrochloride; the antipsychotic medications, acetophenazine maleate, chlorpromazine hydrochloride, chlorprothixene, chlorprothixene hydrochloride, clozapine, fluphenazine decanoate, fluphenazine enathrate, fluphenazine hydrochloride, haloperidol decanoate, haloperidol, haloperidol lactate, lithium carbonate, lithium citrate, loxapine hydrochloride, loxapine succinate, mesoridazine besylate, molindone hydrochloride, perphenazine, pimozide, prochlorperazine maleate, prochlorperazine, prochlorperazine edisylate, promazine hydrochloride, risperidone, thioridazine, thiolidazine hydrochloride, thiothixene, thiothixene hydrochloride, and trifluoperzine hydrochloride; the sedative-hypnotic medications, amobarbital, amobarbital sodium, aprobarbital, butabarbital, chloral hydrate, chlordiazepoxide, chlordiazepoxide hydrochloride, clorazepate dipotassium, diazepam, diphenhydramine, estazolam, ethchlorvynol, flurazepam hydrochloride, glutethimide, hydroxyzine hydrochloride, hydroxyzine pamoate, lorazepam, methotrimeprazine hydrochloride, midazolam hydrochloride, non prescription, oxazepam, pentobarbital sodium, phenobarbital, phenobarbital sodium, quazepam, secobarbital sodium, temazepam, triazolam, and zolpidem tartrate; the stimulants, dextroamphetamine sulfate, methamphetamine hydrochloride, methylphenidate hydrochloride, and pemoline; and the anti-hypertensive, clonidine.

Compounds of the invention may also be administered in combination with a psychological intervention. In one embodiment, therapeutic treatment is combined with cognitive behavioral treatment for insomnia because insomnia is a common complaint of subjects suffering from marihuana withdrawal. Psychological intervention for insomnia provides a safe, effective alternative to pharmacotherapy. Cognitive Behavioral Therapy (CBT) (Morin *Insomnia: Psychological Assessment and Management.* Guilford Press, New York, 1993; Morin et al. Clin Psychol Rev 1996, 16:521-542) includes the following treatment components:

Behavior Therapy: To change maladaptive sleep habits

Cognitive Therapy: To reframe dysfunctional beliefs and attitudes

Education: To promote good sleep hygiene practices

Medication: To facilitate discontinuation of hypnotic medications

The behavioral component typically includes one or more of stimulus control and sleep restriction techniques (Bootzin Proceedings of the American Psychological Association, 1972, 7:395-396; Bootzin et al. *Progress in Behavior Modification* New York: Academic Press 1978, Vol. 6, pp. 1-45; Spielman et al. Sleep 1987, 10:45-56). Exemplary stimulus control instructions include:

1. Lie down intending to go to bed at night only when you are sleepy. Do not adhere to an arbitrary set bedtime.
2. Use the bed/bedroom for sleep and sex only. Do not watch TV, listen to the radio, eat, or read in bed.
3. Get out of bed if you cannot fall asleep or go back to sleep within an estimated 10-15 minutes (do not look at the clock); return to bed only when you feel sleepy, with the intention of seeing if sleep happens, rather than the intention of "trying" actively to fall asleep.
4. If you still cannot fall asleep, repeat step 3 as often as is necessary during the night.
5. Set your alarm and maintain a regular arising time in the morning, irrespective of how much sleep you got during the night, or how tired you may feel. Do not lie in bed awake.
6. Do not nap during the day.
7. Follow these steps consistently, recognizing that it is difficult to change any behavior, and change takes time.

Exemplary sleep hygiene recommendations include:

1. Caffeine is a stimulant and should be discontinued 4-6 hours before bedtime.
2. Nicotine is a stimulant and should be avoided near bedtime and at awakenings.
3. Alcohol is a depressant that can facilitate sleep onset but can disrupt sleep later in the night. It should be avoided in close proximity to bedtime.
4. A heavy meal too close to bedtime can interfere with sleep and should be avoided. A light snack is acceptable.
5. Regular exercise in the late afternoon or early evening may deepen sleep, while exercise too close to bedtime may disrupt sleep.
6. Minimize light, noise, and excessive temperature during sleep.
7. Do not look at the clock when awake at night; this only serves to heighten anxiety and frustration about not sleeping.
8. Establish a 20-30 minute regular "worry time" during the daytime. Find a quiet place, relax, let worries come, and address them at this time, instead of at bedtime. This practice can help decrease worry and mind-racing at bedtime, by re-routing this kind of thinking to a time during the day.

The second component includes cognitive restructuring and is based on the rationale that insomniacs tend to have more anxious affect, worrisome cognitive style, and negative, maladaptive thoughts regarding sleep which adversely effect sleep (Borkovec et al. J. Abnormal Psychology 1981, 90:607-609; Kales et al. *Evaluation and Treatment of Insomnia* New York: Oxford University Press 1984; Van Egeren et al. Journal of Behavioral Medicine 1983, 6:217-232). Their expectations about sleep need and the consequences of insomnia are often unrealistic or invalid. These dysfunctional cognitions are associated with sleep disturbance in that the maladaptive thoughts produce emotional arousal that perpetuates insomnia. The focus of cognitive restructuring to treat insomnia is to alter the underlying dysfunctional thought processes and associated affective responses to produce more healthy, realistic thoughts about sleep and insomnia, thereby decreasing the emotional arousal which can lead to insomnia.

The third element of the approach addresses the lifestyle and environmental factors that can adversely affect sleep. Sleep hygiene instructions are conveyed in a common sense approach with the goal of helping insomniacs better manage these factors such that they optimize rather than deter from sleep.

The fourth component involves medication management and withdrawal. Chronic hypnotic use undermines the development of self-management skills to cope with insomnia. A schedule of gradual titration from sleep aids at the beginning of the cognitive-behavioral treatment program is advocated.

The program is typically brief in duration, inexpensive, and effective. It can be performed in group or individual format. Cognitive-behavior therapy for insomnia provided on an individual basis may produce superior results than group therapy, although there are advantages to the group format. The program typically consists of ten total sessions, the first two of which are devoted to thorough assessment, essential for successful triage and therapy. One focus of the multi-modal approach is helping insomniacs to develop a greater sense of self-efficacy about managing their own sleep difficulties. The sessions of treatment serve to consolidate treatment gains, integrate the therapies, and instruct patients as to how to avoid and cope with potential problems and relapse. With these therapy tools and relapse prevention strategies, patients gain the confidence and ability to address their insomnia and to see it as an inconvenience to be dealt with, rather than feeling victim to it and its effects on all other aspects of their lives.

In addition, subjects undergoing treatment with therapeutic compounds may be enrolled in psychological treatment programs, such as Group Drug Counseling. General group counseling is non-specific "talk therapy" during which a number of elements of the person's life are discussed with no emphasis on the marihuana abuse. Such efforts often serve as a control for meeting with a therapist.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A method of ameliorating or suppressing marihuana dependence, withdrawal or usage, said method comprising administering to a human in need thereof a therapeutically-effective amount of a compound selected from the group consisting of a cytidine-containing compound, a cytosine-containing compound, and a creatine-containing compound.

2. The method of claim 1, wherein said compound administered is cytidine.

3. The method of claim 1, wherein said compound administered is said cytidine-containing compound further comprising choline.

4. The method of claim 1, wherein said compound administered is CDP-choline.

5. The method of claim 4, wherein said CDP-choline is administered orally.

6. The method of claim 1, wherein said cytidine containing compound administered is CDP.

7. The method of claim 1, wherein said administering is chronic.

8. The method of claim 1, wherein said human is a child or adolescent.

9. The method of claim 1, wherein said human is pregnant.

10. The method of claim 1, further comprising administering a psychological intervention to said human.

11. The method of claim 1, wherein craving is reduced.

12. The method of claim 1, wherein said human is diagnosed with marihuana withdrawal or dependence.

13. A method of treating or suppressing marihuana dependence, withdrawal or usage, said method comprising administering to a human diagnosed with marihuana dependence, withdrawal or usage a therapeutically-effective amount of a compound selected from the group consisting of a cytidine-containing compound, a cytosine-containing compound, and a creatine-containing compound.

14. The method of claim 13, wherein said compound administered is said cytidine-containing compound.

15. The method of claim 14, wherein said compound administered is CDP-choline.

16. The method of claim 13, further comprising administering a psychological intervention to said human.

17. The method of claim 13, wherein said administering is chronic.

18. The method of claim 13, wherein craving is reduced.

19. The method of claim 13, wherein said human is diagnosed with marihuana withdrawal or dependence.

* * * * *

UNITED STATES PATENT AND TRADEMARK OFFICE
CERTIFICATE OF CORRECTION

PATENT NO. : 7,947,661 B2
APPLICATION NO. : 11/659924
DATED : May 24, 2011
INVENTOR(S) : Lukas et al.

It is certified that error appears in the above-identified patent and that said Letters Patent is hereby corrected as shown below:

Title Page 3, Item (56) under OTHER PUBLICATIONS, in Katzung et al., replace "Pharmacolgy" with --Pharmacology--;

Under OTHER PUBLICATIONS, in Lukacsko et al., replace "*Pharmocol.*" with --*Pharmacol*--.

Title Page 4, Item (56) under OTHER PUBLICATIONS, in Regenold et al. (2008), replace "Multliple" with --Multiple--.

Title Page 5, Item (56) under OTHER PUBLICATIONS, in Yoon et al., replace "Neurophyschopharmacology" with --Neuropsychopharmacology--.

At Column 1, following the TITLE, please insert the following section:

--STATEMENT REGARDING FEDERALLY SPONSORED RESEARCH

This invention was made with Government support under Grant No. DA11098 awarded by the National Institutes of Health. The Government has certain rights in the invention.--.

Column 7, Line 3, replace "intracistemal" with --intracisternal--.

Column 8, Line 11, replace "antipyschotic" with --antipsychotic--.

Signed and Sealed this
Nineteenth Day of March, 2013

Teresa Stanek Rea
*Acting Director of the United States Patent and Trademark Office*